United States Patent [19]

Goto et al.

[11] Patent Number: 5,541,336
[45] Date of Patent: Jul. 30, 1996

[54] HERBICIDAL TETRAZOLINONES

[75] Inventors: Toshio Goto, Shimotsuga-gun; Seishi Ito, Oyama; Yukiyoshi Watanabe, Saitama; Shin-ichi Narabu, Yuki; Akihiko Yanagi, Tochigi, all of Japan

[73] Assignee: Nihon Bayer Agrochem K.K., Tokyo, Japan

[21] Appl. No.: 403,168

[22] Filed: Mar. 10, 1995

[30] Foreign Application Priority Data

Mar. 18, 1994 [JP] Japan ................... 6-072847

[51] Int. Cl.$^6$ .............. C07D 257/04; A01N 43/713
[52] U.S. Cl. ........................... 548/251; 504/261
[58] Field of Search .................. 548/251; 504/261

[56] References Cited

U.S. PATENT DOCUMENTS

| | | | |
|---|---|---|---|
| 4,618,365 | 10/1986 | Covey et al. | 71/92 |
| 4,826,529 | 5/1989 | Covey et al. | 71/92 |
| 4,830,661 | 5/1989 | Covey et al. | 71/92 |
| 4,956,469 | 9/1990 | Covey et al. | 548/251 |
| 5,003,075 | 3/1991 | Covey et al. | 548/251 |
| 5,136,868 | 8/1992 | Theodoridis | 548/251 |

FOREIGN PATENT DOCUMENTS

| | | |
|---|---|---|
| 0146279 | 6/1985 | European Pat. Off. . |
| 0202929 | 11/1986 | European Pat. Off. . |
| 0578090 | 1/1994 | European Pat. Off. . |
| 0612735 | 8/1994 | European Pat. Off. . |

OTHER PUBLICATIONS

Chemical Abstracts, vol. 108, p. 241, abstract No. 163178b (1988).

*Primary Examiner*—David B. Springer
*Attorney, Agent, or Firm*—Sprung Horn Kramer & Woods

[57] ABSTRACT

Novel herbicidal tetrazolinones of the formula

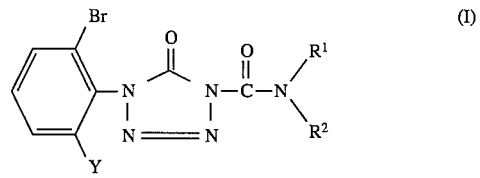

wherein
 Y is hydrogen, bromine or methyl,
 $R^1$ is ethyl or n-propyl, and
 $R^2$ is cyclopentyl or cyclohexyl, with the proviso that the total number of carbon atoms in $R^1$ and $R^2$ is 7 or 8.

The new tetrazolinones may be mixed with other herbicides.

7 Claims, No Drawings

HERBICIDAL TETRAZOLINONES

The present invention relates to novel tetrazolinones, to a process for their preparation, and to their use as herbicides, especially as paddy-herbicides.

It has already been disclosed that tetrazolinone derivatives have herbicidal properties (see U.S. Pat. Nos. 4,618, 365; 4,826,529; 4,830,661; 4,956,469; 5,003,075; 5,019,152 and 5,136,868 or the corresponding European Applications EP-A-146,279 and EP-A-202,929; further see EP-A-571, 854, EP-A-571,855, EP-A-572,855 and EP-A-578,090).

There have now been found novel tetrazolinones of the formula (I)

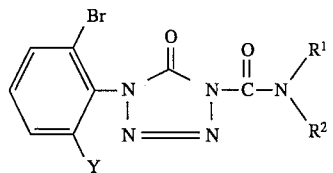

wherein

Y is hydrogen, bromine or methyl, $R^1$ is ethyl or n-propyl, and $R^2$ is cyclopentyl or cyclohexyl, with the proviso that the total number of carbon atoms in $R^1$ and $R^2$ is 7 or 8.

The compounds of the formula (I) can be obtained by a process in which compounds of the formula (II)

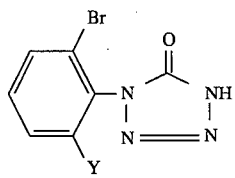

wherein

Y has the same meaning as mentioned above, are reacted with compounds of the formula (III)

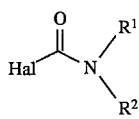

wherein $R^1$ and $R^2$ have the same meanings as mentioned above, and

Hal is a leaving group such as chlorine, bromine, or the like, in the presence of an inert solvent and, if appropriate, in the presence of an acid binder.

The novel tetrazolinones (I) exhibit powerful herbicidal properties, in particular against paddy-field weeds.

Suprisingly, the instant compounds of the formula (I) exhibit a substantially much greater herbicidal action against paddy-weeds than those compounds specifically shown in the references cited hereinabove.

Among the compounds of the formula (I), according to the invention, preferred compounds are those in which Y is hydrogen or methyl.

Specifically, the following compounds, in addition to the compounds mentioned in the examples hereinbelow are of interest:

1-(2-bromophenyl )-4-(N-cyclopentyl-N-ethylcarbamoyl) -5(4H)-tetrazolinone, 1-(2-bromophenyl )-4-(N-cyclopentyl-N-n-propylcarbamoyl) -5(4H)-tetrazolinone, 1-(2-bromophenyl)-4-(N-cyclohexyl-N-ethylcarbamoyl) -5(4H)-tetrazolinone, 1-(2-bromo-6-methylphenyl)-4-(N-cyclopentyl-N-propylcarbamoyl) -5(4H)-tetrazolinone, and 1-(2-bromo-6-methylphenyl)-4-(N-cyclohexyl-N-ethylcarbamoyl) -5(4H)-tetrazolinone.

If use is made, in the above-mentioned process, of 1-(2-bromophenyl)-5(4H)-tetrazolinone and N-cyclohexyl-N-ethylcarbamoyl chloride, as the starting materials for example, the reaction can be expressed by the following reaction equation:

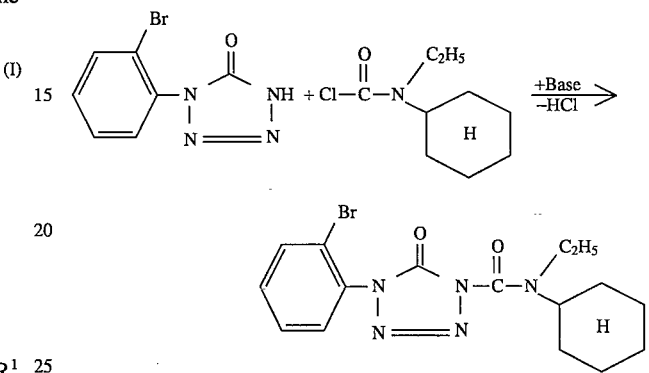

The starting compounds of the formula (II) can be prepared in the manner similar to that described in "The Journal of Organic Chemistry", Vol. 45, No. 21, 1980, pages 5130–5136 or "The Journal of American Chemical Society", Vol. 81, No. 7, 1980, pages 3076–3079 .

As examples of compounds of formula (II), there may be mentioned the following:

1-(2-bromophenyl)-5(4H)-tetrazolinone, 1-(2-bromo-6-methylphenyl)-5(4H)-tetrazolinones, and 1-(2,6-dibromophenyl)-5(4H)-tetrazolinone.

The compounds of the formula (III) are well known in the field or organic chemistry. As specific examples thereof, there may be mentioned:

N-cyclopentyl-N-ethylcarbamoyl chloride,

N-cyclopentyl-N-n-propylcarbamoyl chloride, and

N-cyclohexyl-N-ethylcarbamoyl chloride.

In carrying out the process mentioned above, use may be made, as suitable diluents, of any inert organic solvents. Examples of such diluents are aliphatic, cycloaliphatic and aromatic, optionally chlorinated, hydrocarbons such as pentane, hexane, cyclohexane, petroleum ether, ligroin, benzene, toluene, xylene, dichlormethane, chloroform, carbon tetrachloride, 1,2-dichloroethane, chlorobenzene, dichlorobenzene, and the like; ethers such as diethyl ether, methyl ethyl ether, diisopropyl ether, dibutyl ether, dioxane, dimethoxyethane (DME), tetrahydrofuran (THF), diethylene glycol dimethyl ether (DGM), and the like; nitriles such as acetonitrile, propionitrile, and the like; acid amides such as dimethyl formamide (DMF), dimethyl acetamide (DMA), N-methylpyrrolidone, 1,3-dimethyl-2-imidazolidinone, hexamethylphosphoric triamide (HMPA), and the like; sulfones and sulfoxides such as dimethyl sulfoxide (DMSO), sulfolane, and the like; and bases such as pyridine.

The above-mentioned process may be carried out in the presence of acid binder, and as acid binders there may be mentioned, for example, inorganic bases including hydroxides, carbonates, bicarbonates, alcoholates, and hydrides of alkali metals, such as sodium hydrogen carbonate, potassium hydrogen carbonate, sodium carbonate, potassium carbonate, lithium hydroxide, sodium hydroxide, potassium hydroxide, calcium hydroxide, sodium methoxide, potassium methoxide, potassium tert-butoxide, lithium hydride, sodium hydride, potassium hydride, and the like; inorganic amides of alkali metals such as lithium amide, sodium amide, potassium amide, and the like; and organic bases including tertiary amines, dialkylaminoanilines and pyridines, such as triethylamine, 1,1,4,4-tetramethylethylenediamine (TMEDA), N,N-dimethylaniline, N,N-diethylaniline, pyridine, 4-dimethylaminopyridine (DMAP), 1,4-diazabicyclo[2,2,2]octane (DABCO), 1,8-diazabicyclo[5,4,0]-undec-7-ene (DBU), and the like. Furthermore, use may be made of organic lithium compounds such as, for example, methyl lithium, n-butyl lithium, sec-butyl lithium, tert-butyl lithium, phenyl lithium, dimethyl copper lithium, lithium diisopropyl amide, lithium cyclohexylisopropyl amide, lithium dicyclohexyl amide, n-butyl lithium·DABCO, n-butyl lithium·DBU, n-butyl lithium·TMEDA, and the like.

In the above-mentioned process the reaction temperature can be varied within a substantially wide range. In general, the reaction is carried out at a temperature of from about −30° C. to about 200° C., preferably from about −20° C. to about 130° C.

Further, the reaction is preferably carried out under normal pressure, although it is also possible to employ a higher or reduced pressure.

When the above-mentioned process is carried out, use may be made, for example, of 1.0 to 1.2 mols of the compound of the formula (III) in a diluent such as acetonitrile, for example, per mol of the compound of the formula (II) in the presence of 1 to 1.2 mols of an acid binder to obtain the desired compound.

The compounds represented by the general formula (I) according to the present invention can be used as herbicides for controlling paddy weeds.

Further, it has been discovered that a specially high herbicidal activity can be exhibited by herbicidal mixed compositions, comprising, as active components, the compounds represented by the general formula (I) according to the present invention, together with at least one of the members selected from the group consisting of herbicidally active sulfonamides, herbicidally active pyrazoles, herbicidally active propionanilides, herbicidally active triazines, herbicidally active carbamates, herbicidally active diphenylethers, herbioidally active pyrimidines and herbicidally active acid amides.

Surprisingly, the herbicidally mixed compositions according to the present invention have been found to exhibit herbicidal effects substantially higher than the sum of the herbicidal effects that can be exhibited individually by the herbicidally active, respective components and, as a result, the concentration of each of the active compounds can be substantially reduced when practicing weed control operations, while at the same time, a wide herbicidal spectrum can be obtained. Further, the herbicidal compositions according to the present invention have been found to expand the period of possible application, for example, in paddy rice cultivation, and exhibit excellent herbicidal effects for a period of from early stage of weed-emergence to weed-growing stage, with prolonged duration of activity and excellent residual effect, as well as phytotoxicity-free, excellent herbicidal effects on rice-plants.

As specific examples of the herbicidal sulfonamides to be employed in the present herbicidal mixed compositions there may be mentioned for example, N-2-biphenylylsulfonyl N'-(4,6-dimethoxy-1,3,5-triazin-2yl -urea, ethyl 5-[3-(4,6-dimethoxypyrimidin-2-yl)ureidosulfonyl]-1-methylpyrazole-4-carboxylate, methyl 2-[3-(4,6-dimethoxypyrimidin-2-yl)ureidosulfonylmethyl]-benzoate, 3-(4,6-dimethoxy--1,3,5-triazin-2-yl)-1-[2-(2-methoxyethoxy)-phenylsulphonyl]urea, N-(2-chloroimidazolo[1,2-a]pyridin-3-yl-sulfonyl)-N'-(4,6-dimethoxy-pyrimidin-2-yl) urea, N'-(4,6-dimethoxypyrimidin-2-yl)-N''-(4-methylphenylsulfonylamino) -N'''-(4-ethoxycarbonyl-1-methylpyrazol-5-yl-sulfonyl)-guanidine, and N-(2-cyclopropylcarbonylphenylsulfamoyl)-N'-(4,6-dimethoxypyrimidin-2-yl)-urea.

The above-mentioned compounds are also well known in the art (see Japanese Patent Publication No. 481/1984, Japanese Patent Laid-open Nos. 112379/1982, 56452/1982, 122488/1984, 38091/1989 and 70475/1989).

As specific examples of the herbicidally active pyrazoles to be employed in the present invention there may be mentioned, for example, 4-(2,4-dichlorobenzoyl)-1,3-dimethylpyrazol-5-yl-P-toluenesulfonate, 2-[4-(2,4-dichlorobenzoyl)-1,3-dimethylpyrazol-5-yl]acetophenone, and 2-[4-(2,4-dichloro-m-tolyl)-1,3-dimethylpyrazol-5-yloxy]-4-methylacetophenone.

As specific examples of the propionanilides to be employed in the present invention there may be mentioned, for example, 2-(β-naphthyloxy) propionanilide, and (RS)-2-(2,4-dichloro-m-tolyloxy) propionanilide.

As specific examples of the herbicidally active triazines to be employed in the present invention there may be mentioned, for example, 2,4-bis (ethylamino)-6-(methylamino)-1,3,5-triazine, and 2-ethylamino-4-(1,2-dimethylpropylamino)-6-methylthio-1,3,5-triazine.

As specific examples of the herbicidally active carbamates there may be mentioned, for example, S-p-chlorobenzyl diethylthiocarbamate, S-1-methyl-1-phenylethyl piperidine-1-carbothioate, and S-benzyl 1,2-dimethylpropyl(ethyl) thiocarbamate.

As specific examples of the herbicidally active diphenylethers to be employed in the present invention there may be mentioned, for example, 2,4,6-trichlorophenyl-4'-nitrophenylether, and 2,4-dichlorophenyl-3'-methoxy-4'-nitrophenylether.

As specific example of the herbicidally active pyrimidines to be employed in the present invention there may be mentioned, for example, methyl 2-[(4,6-dimethoxy-2-pyrimidinyl)oxy]-6-[1-(methoxyimino) -ethyl]-benzoate.

As specific example of the herbicidally active acid amides to be employed in the present invention there may be mentioned, for example, (RS)-2-bromo-N-(α,α-dimethylbenzyl) -3,3-dimethylbutylamide.

The above-mentioned active compounds are known to be herbicidally active and are disclosed in "Pesticide Manual", 1991 published by The British Crop Protect Council.

A example of herbicidally active pyrimidines is one known compound that is described ion BCPC Weeds 1993, Brighton, Nov. 22–25th, 1993, Vol. 1., Ref. 2-b.

In the herbicidal mixed compositions according to the present invention, the mixing weight ratio of the active components may be varied over a relatively wide range.

In general, use may be made, per part by weight of the compounds represented by the general formula (I), of the herbicidal sulfonamides in from 0.01 to 2 parts by weight, preferably from 0.05 to 1 part by weight; the herbicidally active pyrazoles from 2.5 to 35 parts by weight, preferably from 3 to 15 parts by weight; the herbicidally active propionanilides in from 0.6 to 50 parts by weight, preferably from 2.0 to 28 parts by weight; the herbicidally active triazines in from 0.06 to 10 parts by weight, preferably from 0.15 to 6 parts by weight; the herbicidally active carbamates in from 3 to 15 parts by weight, preferably from 5 to 10 parts by weight; the herbicidally active diphenylethers in from 5 to 35 parts by weight, preferably from 7 to 15 parts by weight; the herbicidally active pyrimidines in from 0.01 to 2 parts by weight, preferably from 0.1 to 1 part by weight; and the herbicidally active acid amides in from 3.5 to 25 parts by weight, preferably from 4.0 to 10 parts by weight, respectively.

The mixed compositions according to the present invention exhibit a strong herbicidal activity. Therefore the above-mentioned compositions may be used as herbicidal compositions and they may be advantageously used particularly as selective herbicidal compositions for paddy rice.

The herbicidal agents and mixed compositions according to the present invention can be applied, for example, to the following paddy weeds:

Dicotyledons of the following-genera: Polygonum, Rorippa, Rotala, Lindernia, Bidens, Dopatrium, Eclipta, Elatine, Gratiola, Lindernia, Ludwigia, Oenanthe, Ranunculus, Deinostema.

Monocotyledons of the following genera: Echinochloa, Panicum, Poa, Cyperus, Monochoria, Fimbristylis, Sagittaria, Eleocharis, Scirpus, Alisma, Aneilema, Blyxa, Eriocaulon, Potamogeton.

The herbicidal agents and mixed compositions according to the present invention can be applied specifically, for example, to the following paddy weeds in paddy fields:

| Botanical names | Latin names |
|---|---|
| Dicotyledons | |
| Rotala indica | *Rotala indica* Koehne |
| False pimpernel | *Lindernia Procumbens* Philcox |
| False loosestrife | *Ludwigia prostrata* Roxburgh |
| Largeleaf ponweed | *Potamogeton distinctus* A. Benn |
| American waterwort | *Elatine triandra* Schk. |
| Dropwort | *Oenanthe javanica* |
| Monocotyledons | |
| Barnyard grass | *Echinochloa oryzicola* vasing |
| Monochoria | *Monochoria vaginalis* Presl. |
| Matsubai | *Eleocharis acicularis* L. |
| Water chestnut | *Eleocharis Kuroguwai* Ohwi |
| Umbrella plant | *Cyperus difformis* L. |
| Mizugayatsuri | *Cyperus serotinus* Rottboel |
| Urikawa | *Sagittaria pygmaea* Miq. |
| Narrowleaf waterplantain | *Alisma canaliculatum* A. Br. et Bouche |
| Bulrush | *Scirpus juncoides* Roxburgh |

However, the application of the herbicidal agents and mixed compositions according to the present invention is not limited to the above-mentioned weeds, but the application can be effected likewise also to other lowland weeds inhabiting paddy fields.

The present herbicidal agents and mixed compositions can be incorporated into any conventional formulations. As the formulations there may be mentioned, for example, a liquid agent, an emulsion, a hydrated agent, a suspension, a powdery agent, a soluble powdery agent, a granular agent, a suspended emulsion concentration, and microcapsules in a polymeric substance.

Those preparations can be prepared through well-known processes. The processes can be effected, for example, by mixing the active compounds with an extender, namely, with a liquid diluent and/or a solid diluent, and if required, with a surfactant, namely, with an emulsifier and/or dispersant and/or a foaming agent.

In using water as an extender, for example, an organic solvent can also be used together as an auxiliary solvent. As liquid diluents there may be mentioned, for example, aromatic hydrocarbons (such as xylene, toluene or alkylnaphthalene, etc.), chlorinated aromatic or chlorinated aliphatic hydrocarbons (such as chlorobenzenes, ethylene chlorides or methylene chloride, etc.), aliphatic hydrocarbons [such as cyclohexane, etc., or paraffins (for example, mineral-oil fractions, mineral or vegetable oils)], alcohols (such as butanol, glycol and ethers and esters thereof, etc.), ketones (such as acetone, methyl ethyl ketone, methyl isobutyl ketone or cyclohexanone, etc.), strong polar solvents (such as dimethylformamide and dimethyl sulfoxide, etc.), and water can also be mentioned as a liquid diluent.

As solid diluents there may be mentioned ammonium salts, and natural soily minerals (such as kaolin, clay, talc, chalk, quartz, attapulgite, montmorrillonite, or diatomite etc.) and soil synthetic minerals (such as highly dispersible silicic acid, alumina, silicate, etc.). As solid carriers for granular agents there can be mentioned powdered and fractionated rocks (such as calcite, marble, pumice stone, meerschaum, dolomite, etc.), synthetic grains of organic or inorganic powders, and fine particles of organic substances (such as saw dust, coconut-shells, corn ear-stems, and tobacco stalks, etc.).

As emulsifiers and/or foaming agents there may be mentioned nonionic and anionic emulsifiers such as, for example, polyoxyethylene fatty acid esters, polyoxyethylene fatty alcohol ethers such as, for example, alkylaryl polyglycol ethers, alkyl sulfonates, alkyl sulfates, aryl sulfonates, etc., and albumin hydrolyzates.

As dispersants, for example, lignin-sulfite waste liquor and methyl cellulose are suitable.

Adhesives or stickers may also be used in the formulations in the form of a powdery agent, granular agent, jambo agent, or emulsion, and as adhesives or stickers there may be mentioned carboxy methyl cellulose, natural and synthetic polymers (such as gum arabic, polyvinyl alcohol, and polyvinyl acetate etc. for example), natural phosphatides (such as cephalins and lecithins), and synthetic phosphatides. Further, as additives there may be also used mineral and vegetable oils.

Colorants may also be used, and as such colorants there may be mentioned inorganic pigments (such as, for example, iron oxide, titanium oxide and Prussian blue), and organic dyes such as, for example, alizarin dyes, azo dyes, and metallic phthalocyanine pigments, and further trace amounts of such materials as salts of iron, manganese, boron, copper, cobalt, molybdenum and zinc.

The formulations contain generally 0.1 to 95% by weight, preferably 0.5 to 90% by weight, of the active compound (s).

In order to control weeds, the active compounds of the herbicidal agents and herbicidal compositions according to the present invention can be used as such, or in the form of formulations thereof, and the mixture can be handled in the form of formulations or in the form of tank-mixtures.

The active compounds according to the present invention can be used as mixtures with other well-known active compounds, that is, with active compounds normally used for paddy fields such as, for example, bactericides, insecticides, plant-growth regulators, plant nutritive agents, soil conditioners, safeners and any other herbicides.

To the herbidical composition according to the present invention there may be added, per part by weight of the herbicidal sulfonamides, from 1 to 200 parts by weight, preferably from 2 to 100 parts by weight, of a safener such as 1-(α,α-dimethylbenzyl)-3-p-tolylurea, for example.

The present active compounds can be used as such, as their formulations or as the use forms prepared therefrom by further dilution thereof, such as in the form of ready-to-use solutions, emulsions, suspensions, powders, wettable powders, pastes and granules.

They may be used in the customary manner, for example by watering, spraying, atomising, dusting, scattering, etc.

The present active compounds can be used either in the pre- or post-emergence period of plants. It is also possible to apply the active compounds into soil before the seeds of plants are sown.

The concentration of active compound used in the present herbicidal agents can vary within a substantially wide range. It depends essentially on the nature of the desired effect. In general, the amounts used as a herbicide are from about 0.01 to about 10 kg of active compound per hectare, preferably from about 0.1 to about 2 kg/ha.

The dosages of the present herbicidal mixed compositions may be varied within a substantially wide range, viz., from 0.1 to 5 kg/ha and preferably from 0.2 to 3 kg of active compounds per ha.

The preparation and use of the active compounds according to the present invention are illustrated by the following examples, which are only illustrative.

EXAMPLES

Synthesis Examples

Example 1

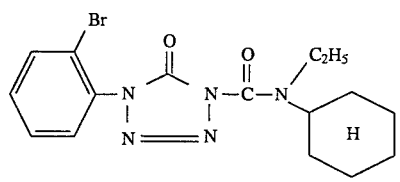
(Compound No. 1)

A suspension of 1-(2-bromophenyl)-5(4H)-tetrazolinone (2 g), 4-dimethylaminopyridine (1.21 g) and N-cyclohexyl-N-ethylcarbamoyl chloride (1.89 g) in toluene (20 ml) was heated at 65°–70° C. for 8 hours. The reaction mixture, when cooled to room temperature, was washed with water and dried over anhydrous sodium sulfate. After the solvent was removed under reduced pressure, the oily residue was subjected to a flush column chromatography (hexane:ethyl acetate=5:2) to give 1-(2-bromophenyl)-4-(N-cyclohexyl-N-ethylcarbamoyl)-5(4H)-tetrazolinone (2.1 g); m.p. 84°–86.5° C.

Further compounds obtainable by the above-mentioned reaction procedure are shown in Table 1.

TABLE 1

| Compound No. | Y | R¹ | R² |
|---|---|---|---|
| 2 | H | $C_2H_5$ | cyclopentyl |
| 3 | H | $C_3H_7$-n | cyclopentyl |
| 4 | $CH_3$ | $C_3H_7$-n | cyclopentyl |
| 5 | $CH_3$ | $C_2H_5$ | cyclohexyl |

(Structure I shown above table: 2-bromophenyl-tetrazolinone-N-C(O)-NR¹R²)

Example 2 (Synthesis of Intermediate Compound)

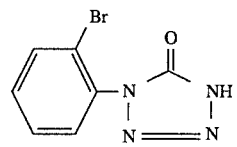

2-bromo-phenylisocyanate (5 g) and trimethylsilylazide (4.36 g) were mixed and refluxed for sixteen hours. The excess of trimethylsilylazide was distilled off under reduced pressure, and to the resulting residue there were added 40 ml of methanol. Thereafter, the solvent was distilled under reduced pressure to give crude product that was then subjected to a flush column chromatography (hexane:ethylacetate=1:1), to obtain the desired 1-(2-bromophenyl)-5(4H)-tetrazolinone (4.1 g) having a melting point in the range of from 142.5° to 146° C.

Biotest Examples

Comparative Examples (According to the Prior Art)

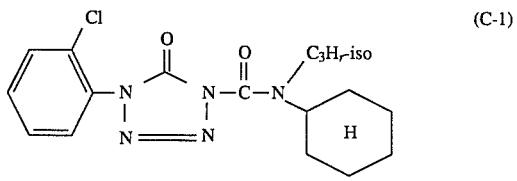
(C-1)

-continued

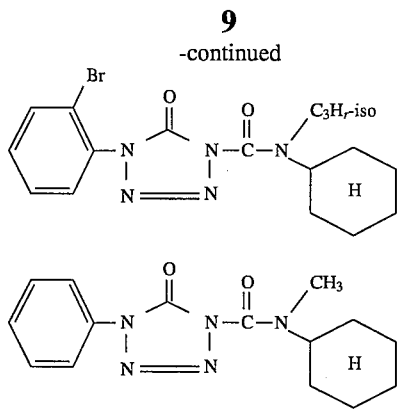

(C-1, C-2 and C-3 are similar to the compounds disclosed in the above-cited prior art documents (see, in particular, U.S. Pat. No. 4,618,365)).

Biotest Example 1

Test on herbicidal activity against lowland weeds

Formulation of Active Compounds

Carrier: 5 parts by weight of acetone

Emulsifier: 1 part by weight of benzyloxy polyglycol ether

To produce a suitable preparation of each of the active compounds, 1 part by weight of an active compound was mixed with the stated amount of carrier and with the stated amount of emulsifier, and the resulting emulsifiable concentrate was then diluted with water to the desired concentrations.

Test Procedure

Aquatic paddy soil was filled in pots (1/2,000 ares), 25×20×9 cm), and rice seedlings (variety: Nipponbare) in the 2.5 leaf stage (plant height about15 cm) were transplanted in two spots at a rate of three per hill.

Seeds of *Echinochloa crus-galli* P.B. var. *oryzoides* Ohwi, *Cyperus difformis* L., *Scirpus juncoides* Roxb., *Monochoria vaginalis* Presl., and annual broad-leaved weeds such as *Lindernia pyxidaria* L., *Rotala indica* Koehne, *Elatine tri- andra* Schk., *Ammannia multiflora* Roxb., *Dopatrium junceum* Hamilt. and so on, were inoculated in the pots.

The soil in the pots was maintained in wet state. Two days later, each pot was watered to a depth of about 2 to 3 cm. Five days after the transplantation of the rice seedlings, a predetermined amount of the active test compounds in the form of an emulsion, prepared in the manner described above was applied on the water-surface of each pot by means of a pipette.

After the treatment, each pot was maintained in the watered state to a depth of about 3 cm.

Three weeks after the treatment, the herbicidal effect and the degree of phytotoxicity were evaluated, wherein 100% indicating the complete death and 0% indicating no herbicidal effect.

The results are shown in Table 2.

TABLE 2

| Active Compound (see synthesis Examples) | Dosage of Active Compound (kg/ha) | Herbicidal effect (%) | | | | | Phytotoxicity (%) Rice (Oryza) |
|---|---|---|---|---|---|---|---|
| | | Echinochloa | Cyperus | Scirpus | Monochoria | Broadleaf weeds | |
| Invention: | | | | | | | |
| 1 | 0.3 | 100 | 100 | 100 | 100 | 100 | 0 |
| | 0.2 | 100 | 100 | 90 | 100 | 90 | 0 |
| Comparative | | | | | | | |
| C-1 | 0.3 | 90 | 100 | 80 | 90 | 60 | 15 |
| | 0.2 | 80 | 90 | 70 | 80 | 50 | 10 |
| C-2 | 0.3 | 90 | 100 | 70 | 90 | 40 | 10 |
| | 0.2 | 60 | 90 | 40 | 60 | 30 | 5 |
| C-3 | 0.3 | 80 | 100 | 70 | 80 | 40 | 15 |
| | 0.2 | 60 | 80 | 40 | 50 | 30 | 10 |

Biotest Example 2

Test for determining herbicidal effect of the present herbicidal compositions on lowland weeds.

In a greenhouse, aquatic paddy soil was filled in pots (1/2,000 ares, 25×20×9 cm), and rice seedlings (variety: Nipponbare) in the 2.5 leaf stage with a height of 15 cm were transplanted in two spots into the pot at a rate of three per hill.

Then, the tubers of *Sagittaria pygmaea* Miq and small pieces of Spikerrush (*Eleocharis acicularis*) as well as the seeds of the following respective weeds were inoculated into the respective pots and filled with water to a height of about 2 to 3 cm above the soil surface:

*Echinochloa oryzicola* vasing,

*Cyperus difformis* L.,

*Monochoria vaginalis* Presl.

Broad leaved weeds such as *Lindernia pyxidaria*, *Rotala indica* Koehne, American waterwort (*Elatine orientalis* Makino), *Ammannia multiflora* Roxburgh, *Dopatrium junceum* Hamilton, Bulrush, *Scirpus juncoides* Roxburgh.

Five days after the transplantation of the rice seedlings, a predetermined amount of the active compounds in the form of an emulsion which had been prepared in the manner mentioned above, was applied on the water-surface of each pot.

After that, the water depth in each pot was maintained at about 3 cm.

Three weeks after application of the active compounds, the herbicidal effect and the degree of phytotoxicity were determined according to the following rating system, wherein 100% indicates the complete death and 0% indicates no herbicidal effect.

The results are shown in the following Table 3:

In Table 3, A, B, C and D in the herbicidal compositions under test represent the following active compounds, respectively:

A: Methyl 2-[3-(4,6-dimethoxypyrimidin-2-yl)-ureidosulfonylmethyl]benzoate,
B: Ethyl 5-[3-(4,6-dimethoxypyrimidin-2-yl)-ureidosulfonyl]-1-methylpyrazole-4-carboxylate,
C: N-(2-chloroimidazolo[1,2-a]pyridin-3-yl-sulfonyl)-N'-(4,6-dimethoxy-2-pyrimidyl)urea,
D: Methyl 2-[4,6-dimethoxy-2-pyrimidinyl)oxy]-6-[1-(methoxyimino)-ethyl]-benzoate.

TABLE 3

| Active Compounds | Dosage of Active Compounds (kg/ha) | Herbicidal Effect (%) | | | | | | | Phytotoxicity (%) Rice (Oryza) |
|---|---|---|---|---|---|---|---|---|---|
| | | Echinochloa | Cyperus | Monochoria | Broadleaf weeds | Scirpus | Sagittaria | Spikerrush (*Eleocharis acicularis*) | |
| 1 + A | 0.10 + 0.075 | 100 | 100 | 100 | 100 | 100 | 100 | — | 0 |
| 1 + B | 0.10 + 0.021 | 100 | 100 | 100 | 100 | 100 | 100 | — | 0 |
| 1 + C | 0.10 + 0.09 | 100 | 100 | 100 | 100 | 100 | 100 | — | 0 |
| 1 + D (*1) | 0.10 + 0.03 | 100 | — | — | — | — | — | — | 0 |
| 1 | 0.10 | 80 | 100 | 80 | 90 | 70 | 0 | — | 0 |
| 1 (*2) | 0.10 | 80 | — | — | — | — | — | — | 0 |
| A | 0.075 | 40 | 100 | 100 | 100 | 100 | 100 | — | 0 |
| B | 0.021 | 50 | 100 | 100 | 100 | 100 | 100 | — | 0 |
| C | 0.09 | 50 | 100 | 100 | 100 | 100 | 100 | — | 0 |
| D (*3) | 0.03 | 80 | — | — | — | — | — | — | 0 |

In Table 3, the composition indicated by (*1) controlled the emergence of Barnyard grass (Echinochloa) for a period of forty-seven days, while the compound No. 1 indicated by (*2) controlled said emergence for a period of forty-five days, and the compound D (*3) controlled said emergence for a period of twenty days.

Formulation Example 1

Water was added to a mixture consisting of 1 part by weight of the above-mentioned active compound No. 1, 0.25 parts by weight of the above-mentioned active compound A, 30 parts by weight of bentonite, 66.75 parts by weight of talc, and 2 parts by weight of lignin sulfonate, followed by an intimate kneading, granulating and drying to obtain granules.

It will be understood that the specification and examples are illustrative but not limitative of the present invention and that other embodiments within the spirit and scope of the invention will suggest themselves to those skilled in the art.

We claim:

1. A tetrazolinone of the formula

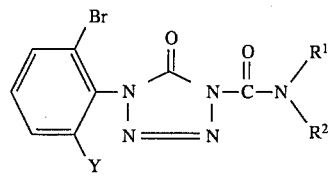

wherein
Y is hydrogen, bromine or methyl
$R^1$ is ethyl or n-propyl, and
$R^2$ is cyclopentyl or cyclohexyl,
with the proviso that the total number of carbon atoms in $R^1$ and $R^2$ is 7 or 8.

2. A compound according to claim 1, wherein Y is hydrogen or methyl.

3. A compound according to claim 1, wherein such compound is 1-(2-bromophenyl)-4-(N-cyclohexyl-N-ethyl-carbamoyl)-5(4H)-tetrazolinone of the formula

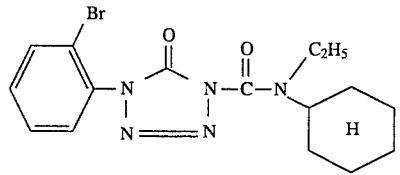

4. A compound according to claim 1, wherein such compound is 1-(2-bromo-6-methylphenyl)-4-(N-cyclopentyl-N-n-propyl-carbamoyl)-5(4H)-tetrazolinone of the formula

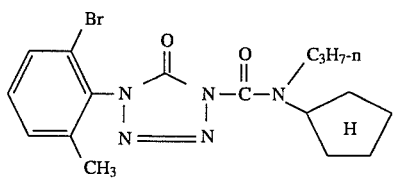

5. A herbicidal composition comprising a herbicidally effective amount of a tetrazolinone according to claim 1 and a diluent.

6. A method of combating unwanted vegetation which comprises applying to such vegetation or to a locus from which it is desired to exclude such vegetation a herbicidally effective amount of a tetratrazoline according to claim 1.

7. The method according to claim 6, wherein such compound is 1-(2-bromophenyl)-4-(N-cyclohexyl-N-ethylcarbomoyl)-5(4H) tetrazolinone or 1-(2-bromo -6-methylpheenyl)-4-( N-cyclopentyl-N-n-propyl-carbamoyl)-5(4H)-tetrazolinone.

* * * * *